United States Patent [19]

Wood

[11] 4,271,696
[45] Jun. 9, 1981

[54] METHOD OF DETERMINING CHANGE IN SUBSURFACE STRUCTURE DUE TO APPLICATION OF FLUID PRESSURE TO THE EARTH

[75] Inventor: Milton D. Wood, Portola Valley, Calif.

[73] Assignee: M. D. Wood, Inc., Palo Alto, Calif.

[21] Appl. No.: 56,065

[22] Filed: Jul. 9, 1979

[51] Int. Cl.³ ............... G01N 19/02; G01N 33/24
[52] U.S. Cl. ............................. 73/37; 33/1 H; 73/432 R
[58] Field of Search ............ 73/37, 784, 432 R; 33/1 H; 166/250

[56] References Cited

U.S. PATENT DOCUMENTS

| | | | |
|---|---|---|---|
| 3,427,652 | 2/1969 | Seay | 166/250 |
| 3,586,105 | 6/1971 | Jonhson et al. | 166/250 |
| 3,739,871 | 6/1973 | Bailey | 166/250 X |
| 3,796,091 | 3/1974 | Serata | 73/784 |
| 3,921,126 | 11/1975 | Waters | 166/250 X |
| 4,044,828 | 8/1977 | Jones et al. | 73/784 X |

Primary Examiner—Gerald Goldberg
Assistant Examiner—Joseph W. Roskos
Attorney, Agent, or Firm—Daniel Silverman

[57] ABSTRACT

This invention relates to a method of determination of the change in subsurface structure of the earth resulting from the application of fluid pressure at a selected point, at a selected depth, in the earth, by measuring at least one physical parameter of the contour of the subsurface of the earth above the point of application of fluid pressure. The method involves positioning a plurality of tiltmeters on the earth above the point of application of fluid pressure arranged in a known array, and measuring the change in angle of tilt of the earth's surface at the point of placement of each sensor while varying the pressure and flow rate of fluid into the earth at the selected point.

17 Claims, 17 Drawing Figures

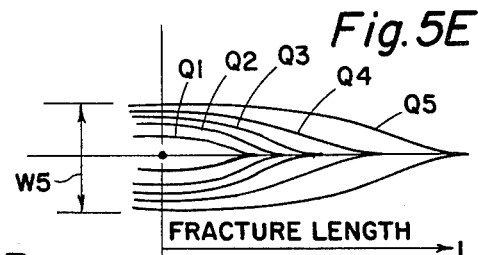
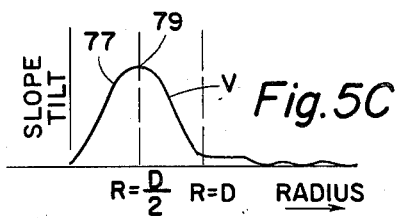
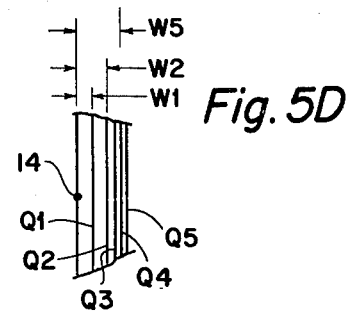
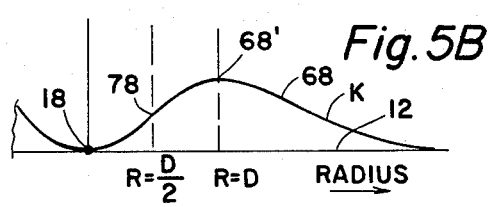
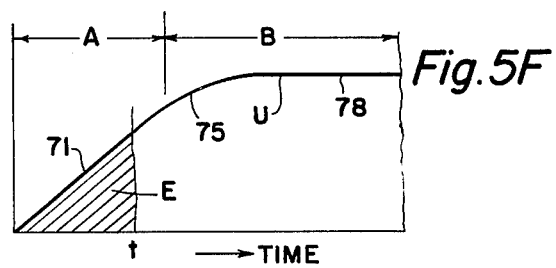
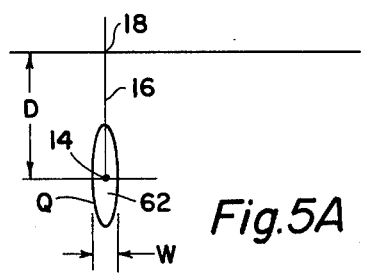
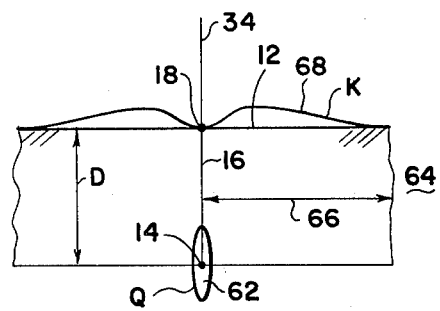

METHOD OF DETERMINING CHANGE IN SUBSURFACE STRUCTURE DUE TO APPLICATION OF FLUID PRESSURE TO THE EARTH

BACKGROUND OF THE INVENTION

1. Field of the Invention

This invention lies in the field of determination of subsurface earth structure resulting from the application of pressurized fluid at one or more known points in the earth, by the determination of the change in surface contour of the earth above the points of application.

More particularly, it concerns the placement on the surface of instruments known as tiltmeters, which are sensitive to the angle of tilt of the earth, after being positioned rigidly in the earth, and leveled. Any change of subsurface structure, such as upward or lateral movement of parts of the subsurface, will be reflected in the surface contour, which can be detected by the tiltmeters. The information of changes in tilt as a function of changes in fluid flow rate and pressure, will provide the basis for determination of subsurface structural change.

2. Description of the Prior Art

In the oil industry for the last 20 or more years, great amounts of money and effort have been devoted to a process known as hydrofracture, which has been, and is now being, employed for the purpose of creating large fractures in the subsurface geological formations. These fractures are propped open so that the elasticity of the rocks and their weight will not cause the fracture to be closed up when the fluid pressure is released. By this means, continuous openings are provided for the flow of liquid and gaseous hydrocarbons through the fracture to the well bore. Thus the hydrocarbons can be recovered more readily than was possible before the fracture was initiated.

However, in spite of the hundreds of thousands of fractures carried out over this period, and in spite of the great effort devoted to finding a method for positively determining the position, the attitude, direction and extent of a fracture, that may have been created in the earth, nothing has resulted to provide such answers. In spite of the fact that many hundreds of thousands of dollars are spent on a single fracture, there is no known way of determining the details of the fracture, if any, other than after an extended period of testing the well, to determine whether its productivity has increased or not. If the productivity is increased, it would indicate the presence of a fracture. However, there is still no way of determining the size, extent, and direction of the fracture.

SUMMARY OF THE INVENTION

It is a primary object of this invention to provide a method and apparatus for determining the change in subsurface structure of the earth by measuring at least one parameter of the surface contour of the earth, at a plurality of known positions before, during, and after the application of high fluid pressure at a selected flow rate to the earth, at a selected depth.

It is a further object of this invention to provide a continuing real-time program in which the flow rate and pressure of fluid application to a selected point in the earth is carried out, while the measurements of tilt angle of the earth are recorded, so that a one-to-one relationship can be shown between the surface physical measurements and a structural change induced into the earth by pressurized fluid application.

The method involves positioning a plurality of instruments, called tiltmeters, in a selected array on the surface of the earth, arranged with due regard to the point of application of the fluid pressure to the earth. The array is adjusted in dimension and configuration as a function of the depth of application of pressure and as a function of the probable structural change expected.

If the geology of the region and in the vicinity of the well bore is known, as is generally the case when a large fracture operation is to be carried out, logical reasoning can be applied to determine what the expected nature of the change in earth configuration would be. On this basis an array is designed and installed prior to the initiation of fluid pressure. The program of fluid application, in pressure and in flow rate is carried out. Simultaneously the measurements of tilt are carried out, and the two series of measurements as a function of time are compared. These data are then interpreted in terms of the required information of the presence of a fracture, its orientation, and its probable dimensions.

BRIEF DESCRIPTION OF THE DRAWINGS

These and other objects and advantages of this invention and a better understanding of the principles and details of the invention will be evident from the following description taken in conjunction with the appended drawings in which:

FIGS. 3 and 4 illustrate the production of horizontal and vertical fractures.

FIGS. 5A, 5B, 5C, 5D, 5E and 5F illustrate various relationships between pressure, flow rate, fracture dimension, etc.

DESCRIPTION OF THE PREFERRED EMBODIMENT

Figure 1:
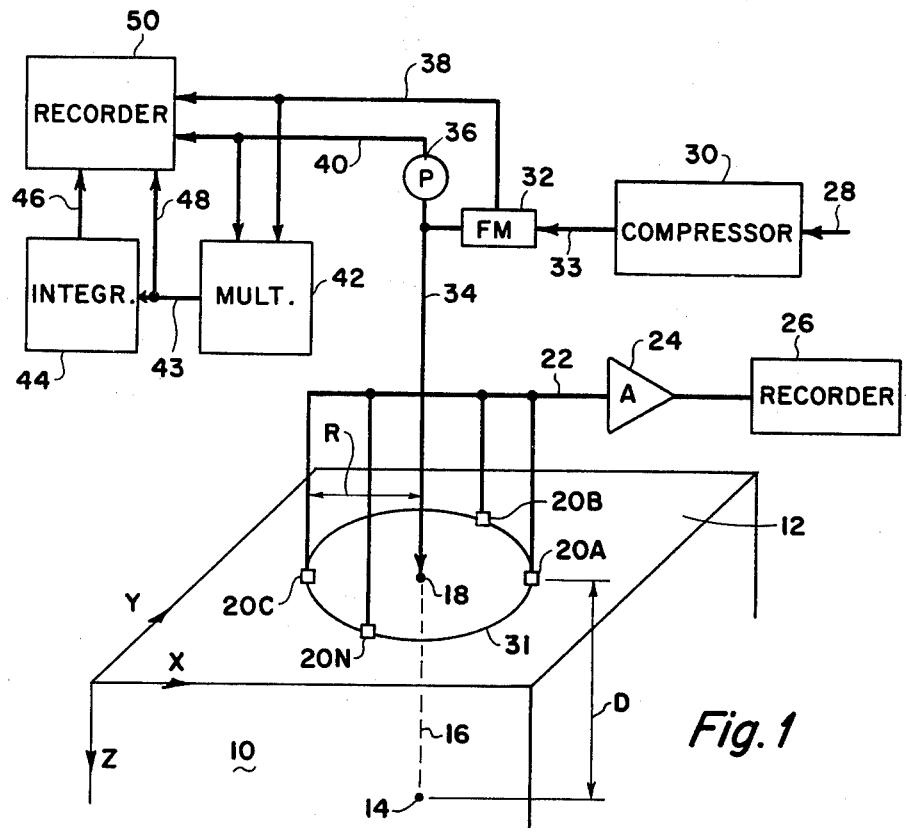
FIG. 1 is a schematic diagram illustrating the method of this invention.

The earth, like most solid materials, is elastic, and follows a stress-strain curve which is linear at least for small amplitudes of dimensional change. It is clear therefore that if a fluid is injected into the earth at a selected point, at a selected depth, and at a selected pressure, as the fluid flows into that point, the earth will expand and form a cavity to contain that fluid. For a homogenous and isotropic solid earth of infinite extent, the cavity would have a spherical shape.

However, the earth is not such a homogenous isotropic body. Quite the contrary, it is a layered, crystalline material, and may contain many small or large fractures, which were formed under prior stress. Furthermore, as a result of geologic deposition and forces, the earth is nominally a horizontally layered solid, with zones of weakness in a direction substantially parallel to the bedding layers of the various geologic formations that comprise the earth.

As a result of this, the void that will be formed in the earth which is occupied by the high pressure fluid may take, and undoubtedly will take, shapes other than a sphere, such as, for example, in the form of lenticular cavities. If the point of application of the fluid pressure is at a relatively shallow depth, it is well known that a lenticular cavity will be formed in a horizontal plane. If the point of application of pressure is at greater depth, the cavity will generally be of lenticular shape and oriented substantially vertically.

Whatever the shape of the void, and of the depth, there is no question but that as say liquid continues to flow into the cavity, the cavity will increase in volume and the surrounding rock material will be compressed. Thus there will be a stress field surrounding the point of application of pressure, which will extend for a considerable distance in all directions, and particularly in the upward direction toward the surface of the earth. There the original contour of the surface of the earth will be modified as a result of the stress field generated by the fluid pressure. Various parameters of the change in contour of the earth's surface could be measured. However, in this invention the preferred parameter to be measured is the change in angle of tilt of the earth's surface, as indicated by a tiltmeter, which is buried in and rigidly supported by the near surface rock material.

On the basis of rock mechanics, it is well known that a fracture will occur in a rock material in a plane perpendicular to the direction of the minimum stress. At shallow depths a point source of pressure will be resisted by a lesser force in a vertical direction than the horizontal direction and thus the fracture will be horizontal. The overburden will be lifted when the applied unit pressure is sufficient to support the weight of the overburden, plus some selected number which depends on the type of rock and so on but is reasonably well-known in the art.

As the depth of the point of application of fluid pressure increases, the overburden pressure increases, and there is a point reached where the weight of the overburden is equivalent to a higher unit pressure than the horizontal resistance to expansion of the central cavity or void, depending on the material constants of the rock. Thus for deep points of application, it is well known that the fractures are more nearly vertical than horizontal.

This process is illustrated in the drawings and in particular by FIG. 1 which represents a portion of the earth, in the form of a cube, the earth being denoted by the numeral 10, with its surface 12 horizontal. A point 50 of injection 14 of fluid pressure is positioned at a selected depth D below a point 18 on the surface. The point of application can ideally be a selected point in the interior of the earth. As a practical matter, however, there is no way of getting the pressurized fluid to that point except by means of a pipe or conduit or borehole from the surface point 18 down to the point of application 14. This conduit is indicated by the dashed line 16. In practice this would be tubing or casing, through which the pressurized fluid would be applied. At the selected depth the fluid probably would be applied through perforations in the casing at the point 14. All of this is well known in the art.

The pressurized fluid may be a pressurized liquid or a pressurized gas. Both of these are commonly supplied for purpose of altering the internal structure of the earth at a selected point. The processes which use these high-pressure fluids comprise the general class of activities denoted by the term hydrofracturing. In most cases, particularly for deep fractures, the fluids used are liquids, particularly liquids which have been thickened, to have an increased viscosity to minimize leakage of the liquid through the porous rock. Thus a pressure can be built up inside of the rock, sufficient to cause fracturing.

In other specialized operations, such as underground combustion, gases such as air under pressure to support combustion have been used. Also, steam has been injected to heat formations containing heavy oil. In other classes of operation, liquids of various chemical composition have been driven through fractures in rocks in order to leach out chemicals, or to chemically attack the rock materials to separate desired chemical elements in the rock and so on. The specific methods and apparatus of these various operations will be discussed in succeeding and separate patent applications, and will not be covered in detail in this application. However, it will be clear that the basic process of applying fluid pressure to the earth at a selected point, at selected pressures and flow rates, and selected fluid composition, for the purpose of changing the structure or chemical condition of the earth will be mirrored in the contour of the surface of the earth and so at least some parameters of the change in structure of the earth can be determined by measuring physical parameters of the deformation or modification of the surface contours.

In FIG. 1 a selected fluid is provided through a pipe 28 to a compressor 30 of known construction and is supplied through a pipe 34 to the vertical conduit 16 in the borehole in the earth, to the point of application 14. The fluid flows through a flow meter FM indicated by the numeral 32 and its pressure is indicated by a pressure meter P, 36. The flow meter 32 and pressure meter 36 may be indicating and recording or may provide electrical signals over leads 38 and 40 respectively, which can go directly to a recorder such as 50, or can be passed to a multiplier 42, whereby the product of pressure and flow rate is determined, which goes by way of lead 48 to a recorder 50. Alternatively, the output of the multiplier 42 which represents the instantaneous product of $P \times F$ goes by lead 43 to an integrator 44 whose instantaneous output goes by lead 46 to the recorder 50. Here P is the instantaneous pressure and F is the instantaneous flow rate.

Thus, it is clear that means are provided for compressing a fluid, which may be a liquid or a gas, measuring the flow rate and pressure under certain controlled conditions, and making a record of all or some of the parameters, such as pressure and flow rate, or the product $P \times F$, or the integral of product $P \times F$. These records are made as a function of time.

Separately, a group of physical parameter sensors 20A, 20B, 20C . . . 20N are arrayed on the surface 12 of the earth in a selected pattern at selected distances from the mouth of the borehole 18. These sensors can be of varied types for measuring mechanical movement of the earth such as displacement vertically or horizontally, or change of angle of tilt of the earth, and so on. Since the frequencies of variation of application of pressure and flow rate will be substantially of low frequency, the measurements at the surface will be substantially static rather than dynamic. The highest frequencies are likely to be in the range of less than one cycle per second.

For the purpose of description of this invention, the instruments 20 will be tiltmeters. They can be of various designs, some of which are of small size and can be inserted into shallow boreholes in the earth so as to provide signals of higher signal-to-noise ratio. Others can be larger and provide higher signal output, which can be placed nearer to the surface and, although subjected to higher noise level from wind and other ground disturbances, may still provide a higher signal-to-noise ratio output than those which are supported in the earth at greater depths. The outputs of these various sensors, or tiltmeters, go by cabling 22, to amplifiers 24, and to recorder 26, as are well known in the art of geophysical measurements, such as seismic prospecting.

The basic process involved can be illustrated in connection with FIG. 1 by selecting a point of application 14 at the bottom of a conduit 16 depending downwardly from a point 18 on the surface of the earth. High-pressure fluid is supplied to the conduit and to the point 14 at selected pressures and flow rates. As a result of the work done in pumping this increasing volume of liquid into the earth at the point 14, the earth is forced to expand and form a cavity at 14. The rock is compressed in all directions around the point 14, which sets up a stress field. As the stress field is formed, it carries to the surface and causes a strain field at the surface in the form of changed contours of the surface as a function of the radial distance from the point 18. The instruments 20 serve to record one parameter of the strain field, namely, the field of tilt of the earth at the surface.

In creating a fracture in the earth, this pressure and flow rate will continue until the pressure gets high enough to force the rock outward to form a cavity.

When the dimension of the cavity is greater than a selected small dimension, it has been observed that there will be a tensile break in the rock, which is called a fracture, and as additional fluid flows into the crack or cavity, the crack or fracture extends itself, sometimes to considerable distances of the order of hundreds of feet from the point 14.

Figures 2A, 2B:
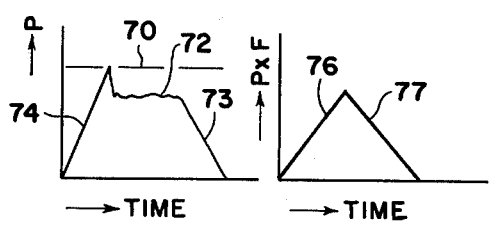
FIGS. 2A, 2B illustrate the variation with time of pressure and of pressure times flow rate.

Referring to FIG. 2A, there is shown a schematic plot which indicates the fluid pressure as a function of time as the fluid is flowed into the earth at the point 14. For convenience the fluid will be considered a liquid. In this discussion it is assumed that the rock is impervious so that there is a 1 to 1 correspondence between the volume of liquid flowed in and the volume of the cavity. This is never the case since there is always some leakage of liquid through the pores of the rock, and in pre-existing fractures and so on. However, as the liquid continues to flow in, the pressure will build up along curve 74, to a peak value 70, at which there will be a rupture of the rock, or a fracture, and the pressure will fall to some lesser value 72. As the volume of the void increases, the length of the fracture increases, although the width of the fracture does not substantially increase.

If as is usual, the liquid does dissipate and flow through the pores and microfractures in the rock, the pressure will eventually drop down to a low value as the pump or compressor is stopped, such as along the curve 73.

Referring now to FIG. 2B, consider that the pump or compressor is started again, and liquid flows such that the product of pressure times flow rate increases as a function of time as 76 in FIG. 2B. As this power application continues, the power supplied to the earth in foot pounds per second would be represented by the product PF, and the deformation of the surface as detected by the detectors 20 would vary linearly with this buildup according to the line 76. If the width of the fracture is sufficiently small, then the surrounding rock will be within its range of linear compression and expansion, and on release of the pressure as in 73 in FIG. 2A, the rock will expand back to its original state and the fracture will close to an insignificantly small dimension. At the same time, the tilt deformation at the surface will be reduced again to zero and substantially the original contour of the earth would return.

This correlation between the surface deformation and the curve of power 76 of FIG. 2B is basic to the operation of the process of this invention.

Figure 3:
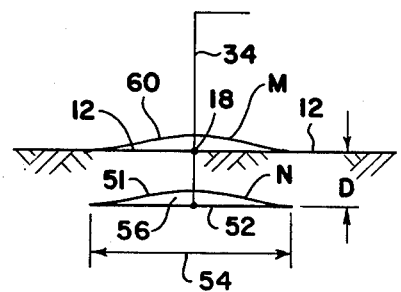

Referring now to FIG. 3, there is shown schematically a cross-section of the earth 10 with surface 12 and a point of application of pressure 14 at a depth D, with fluid applied under pressure through the conduit 34 to the surface at the point 18 and through 16 to 14. The original contour of the earth is assumed horizontal at the point 18. However, as the volume of liquid pumped into the earth at point 14 increases, a lenticular cavity 56 is formed, and the original plane surface 52 is broken, and the opposite surface 58 rises in a domed shape. This shape is characteristic of this type of fracturing, which will be identified by the numeral N. As a result, the overburden layer of depth D will rise with the roof 58, in a characteristic contour of shape M, numeral 60. This is called a horizontal fracture, and, as has been previously mentioned, occurs when the depth D is less than a selected range of dimension, usually of the order of about 1,000 to 1,500 feet.

Referring now to FIG. 4, which is a schematic diagram of a section of the earth 10 similar to that of FIG. 3, but the depth D is now considerably larger than that of FIG. 3. The type of fracture void identified by the letter Q is a lenticular shape, shown here in cross-section with the length of the fracture being perpendicular to the plane of the drawing. This is called a vertical fracture and is formed because the resistance to outward movement of the walls of the void 62 in the direction 66 is less than is the resistance to lifting of the overburden through the much greater depth D. Thus the fracture is preferentially in the vertical direction.

As the void 62 increases in width around the point 14, which is supplied with pressurized liquid through the conduits 34 and 16, the width of the void will increase and thus will set up a stress field in the earth on each side of the void 62. The stress field will be higher in the vicinity of the point 14 than it will be at some distant point 64 at which the stress will be nominal, or zero, depending how far the distance 66 turns out to be.

This stress field in the vicinity of the void 62 extends up to the surface and because the surface is unsupported, there will be a "bulging" of the rock above the original surface 12 of the earth. The earth will take on a shape of a figure of revolution of the characteristic curve K which would be zero directly at the point 18, and rise to a peak 68 at some radius from the point 18 and then decrease to zero out at the distance 64.

Comparison of the shapes of the dome M and the characteristic shape K, indicates the basic differences of the surface expression as a result of a horizontal and of a vertical fracture.

As pointed out in FIG. 2B, as the volume of fluid forced into the cavities 56 and 62 increases, the dimensions of the cavity will increase, and the characteristic shapes M and K will vary in vertical dimension but will be characteristically the same.

It is important to point out that the widths of the cavities 56 and 62 are very small dimensions, usually in the range of 1/16 to ⅛ of an inch or less. The change in dimensions observed in the characteristic surfaces M and K will be even smaller. Thus, the change in tilt which is necessary to measure will be extremely small, and generally will lie in the order of about 1 microradian. However, there is at least one commercial instrument available on the market which can be purchased off the shelf, that can make measurements of this minute value. It has been used in field operations making such measurements from which the characteristic shapes of M and K have been determined, indicating the presence of a horizontal or of a vertical fracture, and providing data from which the dimensions of these fractures can be determined.

Referring now to FIGS. 5A, 5B, 5C, 5D, 5E, and 5F, FIGS. 5A and 5B are in a sense a repetition of FIG. 4. FIG. 5A shows the characteristic lenticular vertical fracture Q of void space 62 at the point 14. The width of the fracture is indicated by the letter W. FIG. 5B again shows the characteristic surface curvature very much exaggerated, denoted by the letter K. This curve K has zero slope directly at the point 18 and rises to a peak at some radius out from the point 18 and then decreases to zero over a considerable distance. Again, the amplitude of the peak 68' of the deformed surface 68 is quite small and the slope of the curve at the point 78 is the maximum 79 on the curve V, 77 of FIG. 5C. The point 78 occurs at a radius R equal roughly to D divided by 2, where D is the depth of the point 14 below the surface.

Examining the shape of the curve 68 between the point 18 and some points at greater radius, the slope of the curve increases according to the curve V of FIG. 5C, and the slope or tilt V of FIG. 5C is the derivative of the curve K. At the point 78, which is at the radius $R = D/2$, the derivative 79 is a maximum, and then curve V falls off roughly to zero at a radius corresponding to the peak 68' of the curve K.

This derivative curve V determines the position of the sensors, the tiltmeters, so that maximum sensitivity will be obtained to vertical fractures. As seen in FIG. 1, the sensors 20 are generally applied in a circular pattern at equal radius from the point 18, and equally spaced on the circle. There may be any number of sensors, four are shown, although 8 or 12 or more can be utilized to obtain a more precise record of the direction or azimuth of the fracture.

FIG. 5D is a great enlargement of the center portion, of the curve Q, denoting the shape of the lens which is the fracture void 62. Only the center vertical portion of the curve Q is shown and only one-half of the void. Q1 represents the wall of the void under a first condition of nominal total work done under pressure P and selected flow volume. If twice the flow volume is pumped, there will be further expansion, and the width of the fracture W will vary from W1 for a first volume, and will increase to approximately double that width W2 for a second increase of a subsequent equal volume which is represented by the wall of the void Q2.

As additional equal volumes of fluid are passed into the fracture, the wall will move outwardly by reduced amounts until it reaches a position Q5 which is substantially the maximum that will be obtained. The reason for this is that as the volume of liquid inserted into the cavity increases, the cavity starts out as a small sphere, and as it goes to a greater radius, it begins to move more into the shape of a lens. When it reaches a certain dimension, it finds that it is easier to separate the rock at a greater distance along the fracture than it is to move the walls of the cavity to a greater width. Thus the cavity or fracture still maintaining a lenticular shape extends itself in a horizontal direction, having reached a maximum width W5 at position Q5.

FIG. 5E is schematic in a similar manner to 5D but is a plan view of a vertical fracture. FIG. 5 indicates that the direction L is the horizontal length of the fracture. Successive incremental volumes of liquid have been inserted into the cavity which first widens in accordance with Q1, Q2, Q3, Q4, and so on until a maximum width W5 is reached, at which the cavity begins to extend itself in accordance with Q4 and Q5 and so on.

This type of action is illustrated in the curve of FIG. 5F where the ordinate of the curve U represents the product of pressure times flow rate which is the power required in forcing the pressurized liquid into the void as a function of time. At the rate of flow F the power required increases along the linear portion 71 of the curve. This zone in which the curve is linear and corresponds to the movement of the walls from zero to say Q2 of FIG. 5D, thereafter the incremental increase in width decreases and the shoulder 75 is formed, after which the curve 78 becomes more or less horizontal as additional liquid is forced in. The additional liquid forces an extension of the cavity along the line L as shown in FIG. 5E. Thus the zone A of the curve U is the zone in which there is substantial linearity between the work done in forcing fluid into the cavity and the response of the cavity itself. Thus the curve U also represents the amplitude of the tiltmeter signal as a function of time.

The cross-hatched space E represents the integral of $P \times F$ over a time t, and this integral E is then proportional to the total energy delivered by the liquid, and to the total deformation, and to the response of the tiltmeter.

This now leads to the basis on which a determination can be made using the set-up as in FIG. 1 in order to determine the azimuth of a vertical fracture at substantial depth below the surface.

Figure 6:
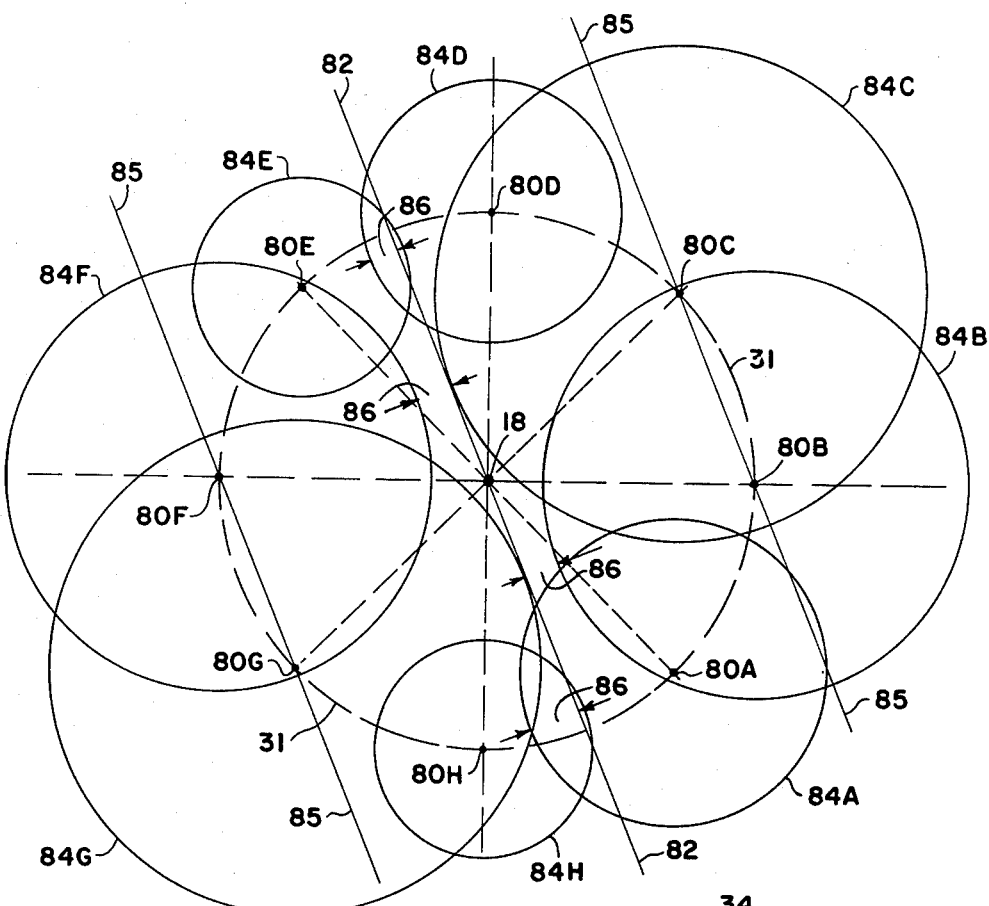
FIGS. 6 and 7 illustrate one method of interpretation of tiltmeter data as regards a deep vertical fracture.

Referring now to FIG. 6, there is shown a dashed circle 31 with center at 18, the point of the mouth of a borehole. A group of stations 80A, 80B, 80C . . . 80G, 80H represent separate tiltmeters. The circles 84 drawn with centers at these points 80 represent the amplitude squared of the maximum signal on the tiltmeter. Thus the radii of the circles represent a quantity proportional to energy which is the integral of the work done in forcing the liquid to compress the rock in order to provide a void of width W. All of the centers 80 are positioned preferably at a radius R equals D/2 so that the reading of the tiltmeter will be maximum for a vertical fracture. A general examination of the drawing shows that the largest circles, 84, representing the largest amplitude squared values, lie generally on two lines which are substantially parallel to a line 82 drawn through the point 18. The points 80A, 80D, 80E and 80H are substantially smaller signals. Since the signal which might be expected to be recorded at a point directly above the fracture, that is at $R=0$, would be a very small signal, it suggests that the fracture then extends somewhere between the two pairs of points 80A–80D compared to 80E–80H.

Another way of expressing this relationship which provides a method of mathematical analysis to determine the direction of the line 82 would be to measure the error between the circles 84A, 84B, 84C . . . 84H, and so on and line 82. The error would be a dimension between the circles and a possible line 82 drawn between them. In other words, the most likely direction of line 82 would be one in which the sum of the squares of the errors 86 between all the circles 84 and a selected trial line 82 would be a minimum. By this means the azimuth of the optimum line 82 can be quickly determined. The finally determined line 82 is representative of the direction or azimuth of the fracture on the basis of the recorded amplitudes of the tiltmeters, as the liquid is pumped in at selected flow rate and pressure. The peak value would be the quantity which is proportional to the integral of P×F to a maximum quantity of flow.

The circular array of tiltmeter locations as in FIG. 6 is a good one, in that the magnitude of the response of each tiltmeter is a function of its position with respect to the azimuth line 82. Those tiltmeters at distance D/2 from the line 82 should show maximum amplitude, while those nearer or farther than D/2 from 82 will show less than the maximum amplitude.

However, other arrays can be used equally well. For example, in FIG. 7 is shown an array with two groups of tiltmeters in two circles, one group 90 of radius R=D/2, the other 92 at radius R=D.

Because 90C is closer to the fracture plane 82 than D/2, its amplitude will be low and its circle 91C should be tangent to 82. The same for 90D and circle 91D. On the other hand, 92B is at greater range than D/2 and its signal should be low, 93B. The signal from 92C, which is substantially at range D/2 should be large, and circle 93C should be tangent to 82. This is further proof of the correct azimuth of 82.

Figure 7:
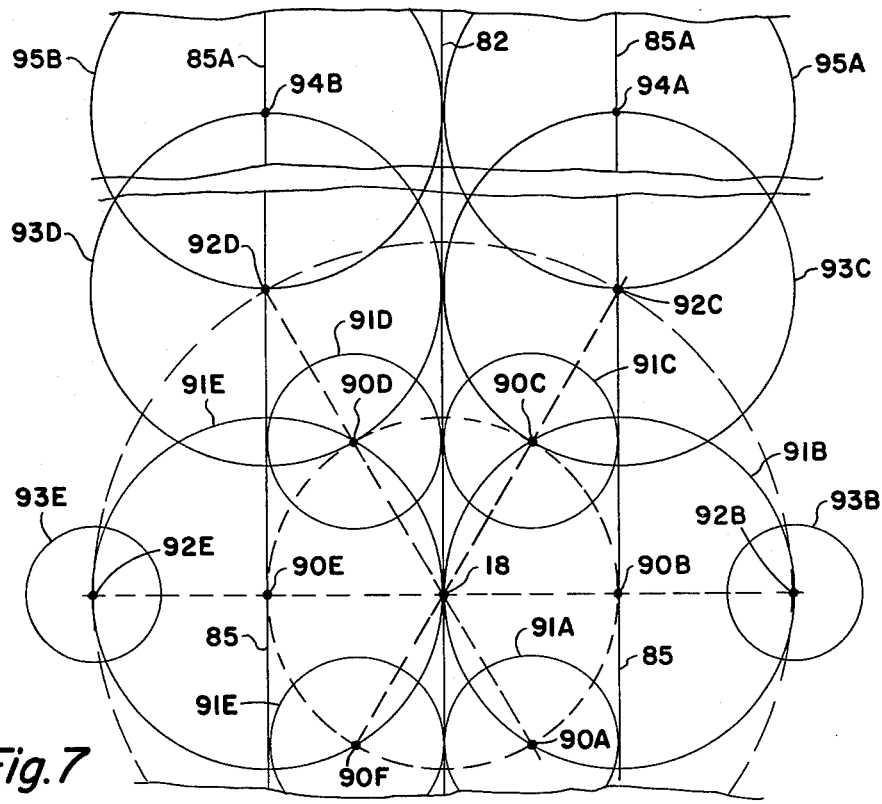

It will be clear that once the fracture is formed and the line 82 is determined as in FIG. 7 then additional tiltmeters can be installed along extension of lines 85, parallel to and spaced from 82 by dimension D/2 and the flow cycle repeated. Examples of this are stations 94A, 94B. If the fracture extends horizontally past stations 94, then the circles 95A, 95B should be tangent to line 82.

Figure 8:
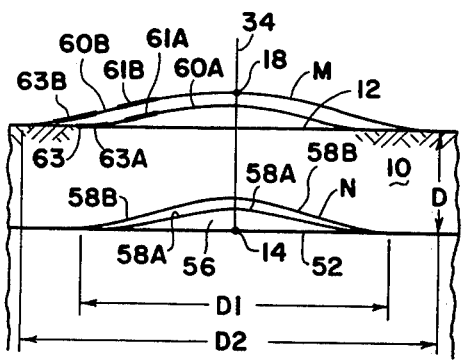
FIG. 8 illustrates one method of interpretation of tiltmeter data as regards a shallow horizontal fracture.

Referring now to FIG. 8, there is shown an enlargement of FIG. 3, showing two positions 58A, 58B of the roof of the cavity 56, and, correspondingly, two positions of the earth's surface 60A, 60B resulting from the cavity 56.

The domed structure M is characteristic of a shallow horizontal fracture 56. The slope or tilt of the earth at point 18 is substantially zero. Off on the flank of the dome M, such as at point 61 the slope would be a maximum at the radius R=D/2.

At greater radius, say point 63, the slope is zero for position 60A of the surface, that is, for position 58A of the roof of the cavity. Then as the liquid flow continues and the diameter D1 of the fracture increases to D2, the slope or tilt of the surface 60B at point 63B increases.

Figure 9A:
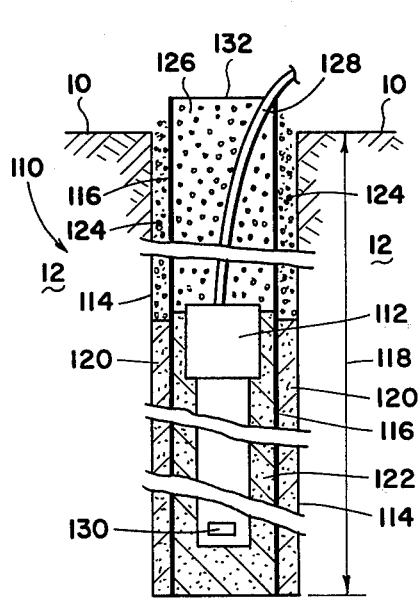
FIGS. 9A and 9B illustrate one method of installing the tiltmeter in the earth.
Figure 9B:
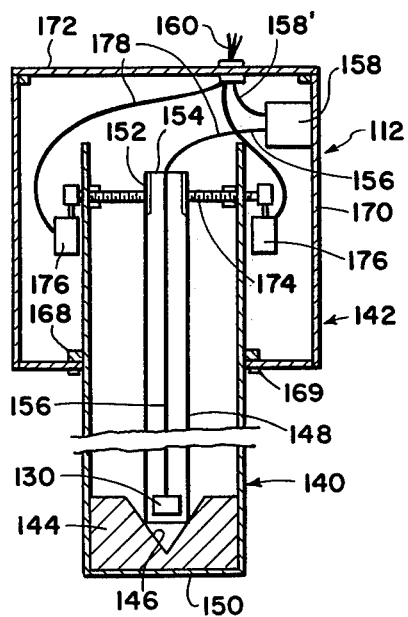

Reference is now made to FIGS. 9A and 9B, which illustrate in cross-section, a shallow portion of the earth 12 with surface 10, indicating the manner in which a tiltmeter instrument, designated by the numeral 130, is planted or positioned in the earth.

The objective is to position the tiltmeter as deep in the earth as is conveniently possible, so that the instrument will respond as closely as possible, to the true tilt of the bedrock, and to be as far away as possible from the very shallow surface layers of the earth that are distrubed by local environmental conditions, such as rain, draught, frost, ice, heavy motor vehicle traffic, etc.

The entire assembly is generally indicated by the numeral 110, and the tiltmeter assembly by the numeral 112.

A shallow borehole is drilled to a depth 118 of the order of 10–15 feet or more, is indicated by the wall 114. A metal casing 116, which is approximately as long as the hole 114 is deep. The casing 116 is closed at the bottom and is positioned securely in the bottom of the hole. This is preferably done by cementing, or with plaster of paris, or can be done reasonably well with packed sand 120 on the bottom and part way up the sides.

The instrument assembly 112 is removably positioned in the bottom end of the metal casing 116. Here sand 122 poured in around the instrument, provides sufficient support for the instrument package 112. The space above the cement or sand 120 in the annulus between the metal casing 116 and the borehole wall 114 is filled with coarse pellets of thermal insulating material 124. Similarly, the space inside of the metal casing 116 and above the instrument package 112 is filled with insulating pellets 126.

The power and control leads 128 are brought up from the instrument package 112 and out the top 132 of the casing 116 to suitable display, recording end control instruments, not shown but well known in the art.

FIG. 9B shows schematically, in cross-section, one embodiment of the tiltmeter instrument package 112. It comprises a principal tubular portion 140, with a larger housing 142 enclosing the top end. The housing can comprise a cylinder, with a suitable opening in the bottom to slide over the tubular portion 140 where it is fastened to ring 168 by means of screws 169.

The tiltmeter instrument 130 is a small cylindrical package manufactured and sold by Rockwell Instrument Co. of Anaheim California. It is identified by the name: Biaxial Tiltmeter.

The tiltmeter is supported rigidly in the bottom of a long, small diameter, thin walled tube 148. The bottom of the tube 148 fits into a conical socket 146 in a block 144. The tube 148 is held in the socket by its own weight. The electrical leaks 156 are carried up inside of the tube 148 and out the top 154. They then go to an amplifying system 158 which is part of the commercial package of the tiltmeter. The output leads 158' then go with the conductor bundle 160.

The top end 152 of the tube 148 is square. There are four levelling screws 174 set into the top of the housing 140 so as to press, one on each of the four faces of the tube 152.

Since this instrument package is intended to be positioned fairly deep in the earth, it is impractical to adjust the levelling screws by hand, so a telemeter control is provided with motors 176 to drive the screws, etc.

The top of the instrument package is marked with each of the two principal axes of the tiltmeter, and means are provided to set the package 112 in a selected azimuth, which is a function of the selected array chosen.

A tiltmeter for this application should have the power to resolve change in tilt to $10^{-7}$ to $10^{-8}$ radians. While the description of FIGS. 9A, 9B are based on one type of tiltmeter, other types could, of course, be used in practicing this invention. Such other tiltmeter would probably require a different method of placement.

While I have used the value of R=D/2=0.5D as the radius of maximum slope, this is not precisely correct. For a halfspace that is homogeneous and isotropic, the theoretical value is 0.38D. However, since the practical earth is not homogeneous or isotropic, a more average value of 0.5D is commonly used.

Thus a radial array of tiltmeters at increasing radius from 18 will indicate by the magnitude of tilt, and also by the time of tilt, as the flow of liquid continues, the horizontal extend D1, D2, etc. of the fracture 56.

By placing tiltmeters at selected radii from point 18, such as at point 63, and observing when the tilt 63A, 63B begins to show, determination can be made that the fracture perimeter has just reached the radius 63.

There is a unique field of surface tilt produced by any pressurized horizontal fracture in the earth. This field is a function of the elastic properties of the earth in the vicinity of the fracture (shear modulus,; Poisson's ratio,), the pressure P in the fracture, and the depth D, and length L, of the fracture.

Figure 10:
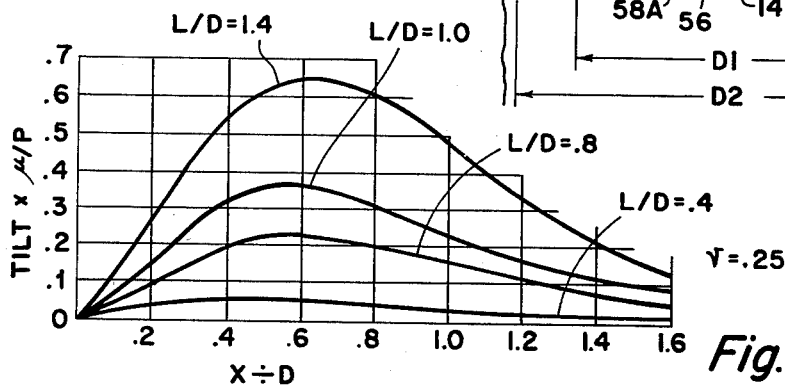
FIG. 10 illustrates the relations between various earth parameters.

In FIG. 10 are shown a family of curves having an ordinate Tilt×shear Modulus pressure, as a function of the distance X, from the mouth of the borehole to the radius of the tiltmeter, divided by P the pressure in the fracturing fluid. Each of the curves is for a different L/D. These curves confirm what was stated in connection with FIG. 8, that is, for a tiltmeter at a fixed distance X, the tilt will be greater, the larger the diameter L of the fracture. These curves were drawn for a Poisson's ratio of 0.25, although similar diagrams can be drawn for other values of Poisson's ratio.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim, including the full range of equivalency to which each element thereof is entitled.

What is claimed:

1. The method of determination of the change in subsurface structure of the earth resulting from the application of fluid pressure at a selected point, at a selected depth, on the earth, comprising the steps of:
    (a) positioning in the earth, near the surface thereof, a plurality of sensors for determining the change in angle of tilt of the earth at the positions of said sensors, in a selected array, of known positions with respect to said point of application of said fluid pressure to the earth;
    (b) applying fluid pressure to the earth at said selected point, at a selected pressure and flow rate; while
    (c) measuring a function of the change in tilt of the earth at said positions of said sensors, and
    (d) from the measured changes in tilt of the earth at the positions of said sensors, determining the structural changes in the earth resulting from said applied flow of fluid.

2. The method as in claim 1 in which said fluid is a liquid.

3. The method as in claim 1 in which said fluid is a gas.

4. The method as in claim 1 in which the depth of said point of application of said fluid is less than 1500 feet.

5. The method as in claim 1 in which the depth of said point of application of said fluid is greater than 1000 feet.

6. The method as in claim 1 in which said array of sensors is at least one linear array.

7. The method as in claim 1 in which said array of sensors is two dimensional.

8. The method as in claim 7 in which said two dimensional array is circular, with the center of said circle substantially directly above said point of application of said fluid pressure.

9. The method as in claim 8 in which the radius of said circle is a selected function of the depth of said point of application below the surface of the earth.

10. The method as in claim 9 in which said radius R is equal to D/2, where D is the depth of said point of application.

11. The method as in claim 1 in which said fluid pressure and flow rate, and said function of said change in tilt are recorded substantially as a function of time, as a selected program of fluid flow rate and pressure is carried out.

12. The method as in claim 11, in which said program includes increasing fluid pressure, and then reducing the fluid flow rate to zero while holding pressure on the earth.

13. The method as in claim 12 including the additional step of reducing applied fluid pressure to zero.

14. The method as in claim 11 in which said program includes the steps of:
    (a) raising the fluid pressure to a high enough value, P1, so that the formation fractures;
    (b) reducing the fluid pressure to a value P2 less than P1; and
    (c) raising the pressure again to a value P3 higher than P2, and close to, but less than P1.

15. The method as in claim 8 in which the axis of maximum sensitivity of said sensor lies in a vertical plane of direction radial to said point of application.

16. The method as in claim 1 in which a borehole is drilled from the surface of the earth to said point of application and said flow of pressurized fluid is conducted through said borehole.

17. The method as in claim 1 in which said sensors are tiltmeters.

* * * * *